United States Patent
Sosnay

[11] 3,975,823
[45] Aug. 24, 1976

[54] ORTHODONTIC TORQUING SYSTEM

[76] Inventor: Alan Jay Sosnay, 55 E. 9th St., New York, N.Y. 10003

[22] Filed: Jan. 21, 1975

[21] Appl. No.: 542,729

[52] U.S. Cl. .................................................. 32/14 A
[51] Int. Cl.² ............................................ A61C 7/00
[58] Field of Search ............... 32/14 R, 14 A, 14 E

[56] References Cited
UNITED STATES PATENTS

| | | | |
|---|---|---|---|
| 3,162,948 | 12/1964 | Gerber | 32/14 E |
| 3,235,965 | 2/1966 | Muir | 32/14 A |
| 3,374,542 | 3/1968 | Moylan, Jr. | 32/14 A |
| 3,416,229 | 12/1968 | Kesling | 32/14 A |

FOREIGN PATENTS OR APPLICATIONS

| | | | |
|---|---|---|---|
| 1,029,981 | 5/1958 | Germany | 32/14 A |

*Primary Examiner*—Louis G. Mancene
*Assistant Examiner*—Jack Q. Lever
*Attorney, Agent, or Firm*—Flynn & Frishauf

[57] ABSTRACT

A torquing spring formed of a wire loop having the top of its central portion adapted to engage the labial surface of the tooth and continuing into a pair of vertically extending legs. Each leg terminates at a pair of axially contiguous coil-sets. One of the coil sets associated with each leg is unrestricted, while the other of the coil-sets associated with each leg is bound to the base arch wire.

30 Claims, 12 Drawing Figures

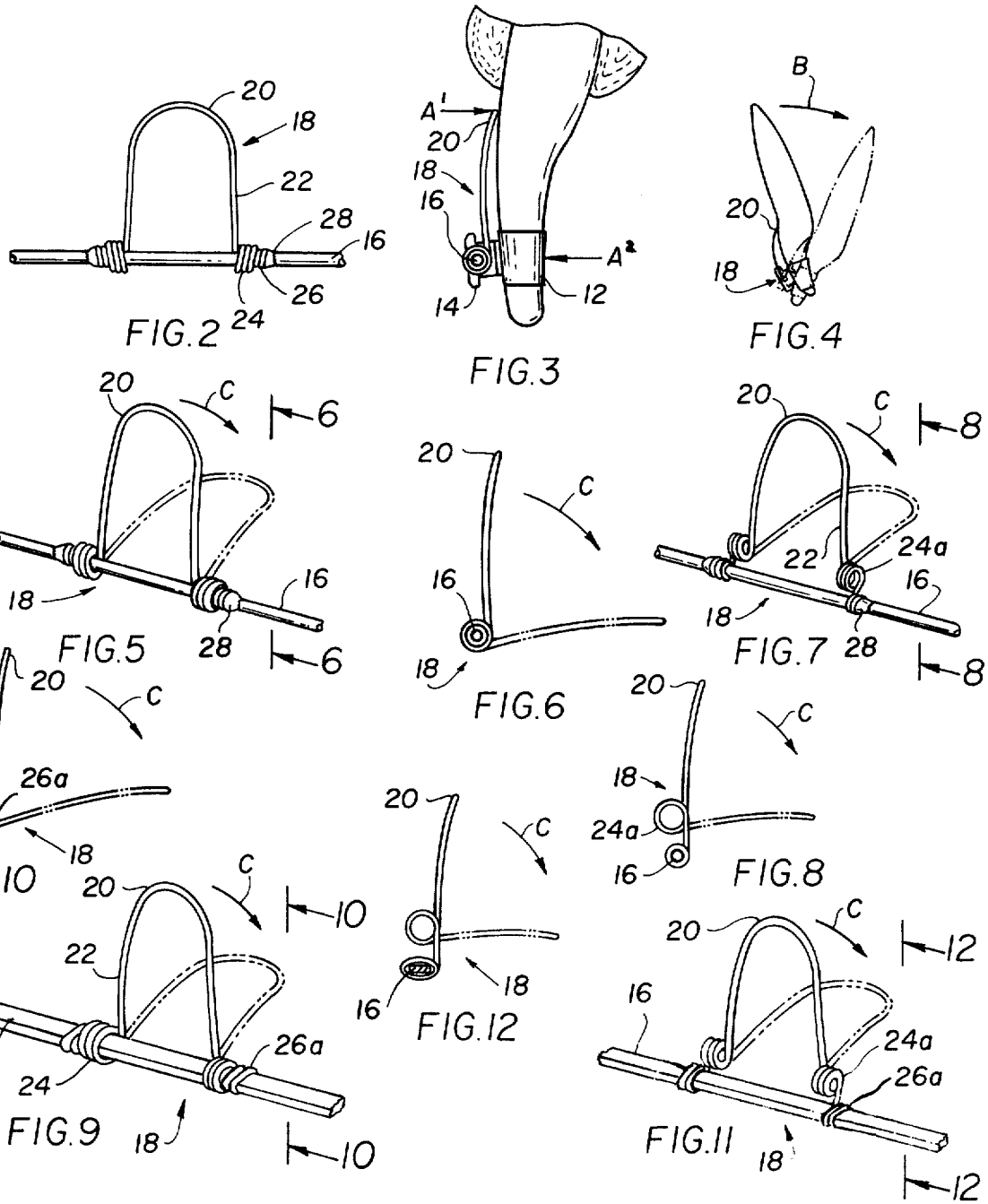

ORTHODONTIC TORQUING SYSTEM

BACKGROUND OF THE INVENTION

The present invention relates to an appliance for straightening and orienting the roots of selected teeth by the application of controlled force moments to their crowns, hence producing a pivoting action.

Many orthodontic treatment techniques in use today move teeth in a two phase procedure. In the initial phase the forces which are applied to the crowns of the teeth produce a greater displacement of the crown than of the root resulting in a tipping movement.

The latter phase employs moments of force which are also applied to the crowns of the teeth in order to upright the roots, thereby placing them in a position of proper axial inclination, commensurate with normal function, favorable esthetics, and stability. This is termed the torquing phase.

Lingual root torque is difficult to achieve particularly on the maxillary anterior teeth. The reason is that all forces must be applied to the crown, while the center of resistance to root movement is located in a remote position along the apical portion of the root surface. This results in a situation of severe mechanical disadvantage.

Several orthodontic appliances are known to provide root torquing. They generally consist of three basic elements: 1) metal bands which circumferentially encompass the crown of each tooth and are attached to them by cementation; 2) brackets of varying configurations (according to technique) which are affixed to the metal bands; and 3) base arch wire — usually of a U-shaped configuration which fit through slots in each of the brackets. The base arch wire is generally round or rectangular in cross-section. In some applications brackets may be attached directly to the tooth surface, without using bands, by means of bonding.

The arch wire may act in an active or passive capacity. In the passive mode it acts as a track along which the teeth are moved. In the active mode deformations are incorporated in the base arch wire during its fabrication. When the arch wire is placed into position within the bracket slots these deformations serve to produce forces and moments which move teeth during orthodontic treatment.

One of the early attempts to produce torquing moments consisted of placing a rectangular arch wire, at an angle, within a rectangular slot of a bracket welded to a band. The angular twisting of the stressed arch wire reacted against the bracket and produced a torquing force on the tooth. This method, while it did produce torque, was most disadvantageous, because of the limited degree of flexibility inherent in the arch wire itself. This produced undesirably high magnitudes of force, often resulting in extreme pain and root resorption. Because of inflexibility of the rectangular arch wire, the force became dissipated rapidly, necessitating frequent adjustments of the arch wire at great discomfort to the patient.

Further attempts followed the line of taking the torsional force from the bracket slot and moving it more cervically on the crown closer to the center of resistance to movement. As a result, several varieties of auxiliary torquing appliances capable of being mounted on the arch wire were developed.

In U.S. Pat. No. 3,325,965 issued to Richard J. Muir, there is described an elongated wire formed into a series of contiguous U-shaped loops separated by coils. The intermediate coils between each of the U-shaped loops are wound in an alternating direction and fit loosely around the axis of the base arch wire. The U-shaped loops extend apically when activated, so that they bear against the labial aspect of the anterior teeth. The elongated wire is provided at each of its distal ends with an expanded occlusal loop which extends from the arch wire in a direction opposite to that of the U-shaped loops previously mentioned, and engages against the buccal aspect of the canine and premolar teeth. Thus any potential moments of force coming from the anterior apical loops are produced by a complicated interaction between the arcuate portion of the base arch wire and the Muir Auxiliary which is initially coplanar with the arch wire and is subsequently distorted during activation. During activation conflicting rotary actions of the individual coils are induced because of the non-parallel nature of the planes of rotation of the several sliding coils. Moreover, forces are induced which attempt to rotate these sliding coils within their individual tangent planes to the arch wire. These motions are restrained by the arch wire within which counter reactions are set up. In addition, reactive forces are introduced through contact of the occlusal loops and posterior teeth. This appliance exhibits the following defects:

1. Because of the multiple contiguous loops and coils the wire system is highly flexible and therefore of minimal effectiveness in producing sufficient moments to obtain the required effects.

2. If however, it were conceivable to produce sufficient moments with this mechanism to lingually torque anterior roots, then undesirable buccal root movement of the anchoring canine and premolar teeth may also result through counteraction. The coils in this device serve as a means of attachment to the base arch wire and are not for helical spring action.

3. If one chooses to argue that the auxiliary appliance exhibits helical coil action, then the auxiliary appliance must be considered as being highly inefficient, since the alternating manner in which the coils are wound result in only every other loop closing in one direction. The intermediate loops open in the same direction, consequently producing an appliance in which only alternate loops may possibly provide torquing movement.

4. The arrangement in this appliance results in excessive expansion of the buccal segments of the base arch wire.

5. The device provides an asymmetric loop system with respect to any individual tooth or group of teeth.

Another attempt, known as the Ford Torquing appliance, is similar to that of Muir in that two apical loops are freely mounted on an arch wire. The apical loops are interconnected by windings about the arch wire. The windings have a bridging portion which is engaged by a small finger-like prong soldered to the arch wire. By rotating the apical loops about the arch wire, the engaging prong becomes torsionally loaded causing a reactive force through the windings upon the apical loops. A significant disadvantage of this configuration is the decreased effectiveness of the spring action on each apical loop, since loading occurs only at the prong region activating only the mesial legs of each loop. This also produces an undesirable asymmetry with respect to each tooth.

Recently, a torsion appliance, known as the Warren Torquing Spring, manufactured by the Rocky Mountain Dental Products Company has come into use. This appliance comprises individual U-shaped torquing springs having each leg terminating in an elliptical coil which is adapted to a sliding fit over a rectangular cross-sectional arch wire. Once placed upon the arch wire all the elliptical turns serve as a rigid anchor, binding the appliance to the arch wire.

Because of the rigid attachment of the elliptical coils to the arch wire at the base of the loop the only spring action is that of a simple cantilever beam provided by the legs of the loop. This construction requires an excessive deflection of the loop by as much as 90°. This leads to permanent deformation of the spring due to lost elasticity. Thus severely diminishing the effectiveness of the appliance.

In these respects the Warren Appliance is no different than the conventional Debnam Torquing Arch manufactured by the Rocky Mountain Dental Products Company wherein two finger-like projections are centrally soldered to the base arch wire forming a cantilevered beam. Debnam's appliance exhibits the same inherent defects in design as the Ford Torquing Arch in that spring action is exerted on only one side of the tooth hence producing an asymmetric force system.

The Kitchton auxiliary torquing device manufactured by T.P. Laboratories, La Porte, Ind., consists of two legs extending from a central coil formed in the plane of the legs. The legs which are initially bent have hooked ends. The coil is anchored on the arch wire and the leg ends are carried down and hooked over the base arch wire. This configuration now forms a pair of apical loops. The orientation of the coil is 90° rotated with respect to any of the previously described coils lying in a plane parallel to the labial face of the maxillary central incisor teeth when activated. The coil serves only as a means of attachment to the base arch wire. Attachment may be achieved by the separation and straddling of the coils over the base arch wire in conjunction with a steel ligature tie through the coil center and around the arch wire. Alternately the coil may simply be placed behind and against the base arch wire and then tied to it by ligation. The coil is located on that portion of arch wire between the central incisor teeth.

In either case the holding action is simply a frictional one and slipping may occur. The coil serves merely to aid in the mode of attachment and doesn't function as a source of spring force against the teeth. Any associated spring action which might occur stems from the interaction of the curved arch wire with the planar apical loop configuration, resulting in undesirable expansive counter forces on the base arch wire.

A similar functioning device is Garcia Torquing Auxiliary manufactured by the Unitek Corporation, of California, which utilizes the same holding principle of friction attachments to the base arch wire. However, it utilizes a hook instead of a coil in its central portion.

It is the object of the present invention to provide an improved orthodontic torquing device overcoming the disadvantages found in the prior art appliances.

It is a further object of the present invention to provide an orthodontic torquing device having an improved spring rate and a continual spring action throughout its use in treatment.

It is an object of the present invention to provide an orthodontic torquing appliance which is of simple and convenient manufacture and which may be utilized with numerous conventional types of orthodontic appliances.

The foregoing objects, other objects, as well as numerous advantages of the present invention will be obvious from the following disclosure.

SUMMARY OF THE INVENTION

According to the present invention the foregoing objects as well as those enumerated hereinafter are obtained by providing an orthodontic torquing device comprising a loop having a pair of legs, each leg of which terminating in a pair of coil-sets. Each of the coil-sets are helically wound and one of the coil sets of each pair, (preferably the outer coil set), is closely associated with and fixedly anchored to the arch wire while the other coil-set of each pair is maintained free of the arch wire and in unrestricted movement with respect to the arch wire.

As a result of this construction, each leg of the apical loop is spring loaded by a freely functioning helical spring formed by the unrestricted coil-set and is anchored by the other coil-set to the base arch wire. The net effect is to produce a highly efficient spring capable of being angularly activated in excess of 90° under constant tensional conditions delivering forces within the optimal range for the movement of roots. The torque magnitude and deflection characteristics of the spring can be closely controlled through appropriate design in making variations in coil size, number of coils and wire size. Further desirable characteristics of the spring are its favorable load-deflection rate and the absence of visible permanent deformation of the spring material, during use.

The device may be attached to either round or rectangular arch wire by soldering the outermost turn of the outer coil-set directly to the arch wire. Alternatively, the outer coil-set may be elliptically shaped and may be slide fit or force fit over a rectangular cross-sectional arch wire. When the apical loop is deflected, these outer elliptical coils bind with the arch wire. In this latter alternative mode, unlike the structures known in the prior art, there is the presence of an inner coil-set that remains unrestricted by the arch wire and that maintains a complete free helical coil spring action.

Another aspect of the present invention lies in the manner in which the outer coils of each leg are affixed to the base arch wire by soldering. The soldering is accomplished in a unique manner by placing a minute arc of solder around the arch wire adjacent to the last winding of each outer coil-set. Flux may then be placed on the outer coils. Portions of the arch wire are heated by electrical resistance causing the solder to melt and flow, thereby anchoring the spring positively to the base arch wire. Since it is only the outer coils which are closely in contact with the arch wire, only they are heated significantly during this process. Therefore, the inner coil-sets, which are of larger diameter and not in close contact with the base arch wire, are not damaged by the heat which is generated.

In the preferred form of the present invention the coil-sets are coaxial with each other and surround the arch wire, however, in one modification of the invention the inner coil set may be offset from the outer coil-set and thereby become positioned exterior to the arch wire. This is accomplished in conjunction with both round and rectangular base arch wires.

Several forms of the invention may furthermore be made. In one instance a plurality of U-shaped torquing springs may be arranged at spaced intervals about the length of the arch wire corresponding to the position of those teeth desired to be moved. This assembly may be constructed as an integral unit resulting in a preformed torquing system freeing the orthodontist from having to fabricate appliances. This is possible due to predictable variances in tooth sizes and spacings, allowing for a limited number of preformed arch sizes. In another situation, the torquing springs may be supplied separately and may be positioned by sliding them onto the base arch wire, in selected positions, determined by the orthodontist himself.

Full details of the present invention are set forth in the following disclosures and are shown in the accompanying drawings.

BRIEF DESCRIPTION OF THE DRAWINGS

In the drawings:

FIG. 1 is a general view of a portion of the denture showing the application of the present invention thereto in the activated state;

FIG. 2 is an enlarged detailed view of a portion of a round arch wire to which the torquing device of the present invention is secured;

FIG. 3 is a sectional view through FIG. 1 taken along lines 3—3;

FIG. 4 is a view illustrating the lingual movement of the tooth, under treatment, with the torquing device of the present invention;

FIG. 5 is a perspective view showing the torquing device seen in FIG. 2;

FIG. 6 is an end view of the embodiment shown in FIG. 5 taken in the direction of line 6—6, showing its angular deflection;

FIG. 7 is a view similar to that of FIG. 5 showing an alternative embodiment of the present invention.

FIG. 8 is an end view of the alternative embodiment shown in FIG. 7 taken along lines 8—8;

FIG. 9 is a perspective view of a torquing device of the type seen in FIG. 2 mounted on a rectangular arch wire;

FIG. 10 is an end view of the embodiment shown in FIG. 9 taken along lines 10—10;

FIG. 11 is a perspective view of the alternate torquing device of FIG. 7 mounted on a rectangular arch wire; and FIG. 12 is an end view of the embodiment shown in FIG. 11 taken along lines 12—12.

DESCRIPTION OF THE INVENTION

FIG. 1 illustrates the application of the present invention to a representative orthodontic appliance, generally depicted by the numeral 10, which is attached to a partially shown maxillary denture of which only the anterior central and lateral incisors and left cuspid are fully seen. The appliance comprises for illustration bands 12 cemented about each tooth, a bracket 14 secured to each band and a base arch wire 16 which conforms in general curvature to that of the denture. The base arch wire 16 is secured to each of the brackets 14 by ligatures, not shown, and terminates at its distal ends within the molar bracket sheaths. The appliance thus, illustrated in FIG. 1, is representative of the general technique for aligning the teeth and includes those elements deemed basic in such techniques as the Edgewise, and the Begg techniques. In these techniques, the form of the brackets, arch wires, ligatures and auxiliary springs etc., may vary. Such variations and differences in the specific forms of these elements will in general have no effect on the application of the present invention.

The torquing device of the present invention, generally depicted by the numeral 18, is adapted to be mounted on the base arch wire, with respect to one or more selected teeth. The torquing device 18 comprises a suitable resilient wire bent into a loop of a generally U-shaped form having a top central portion 20, a pair of legs 22, each leg of which terminates in a pair of coil-sets 24 and 26 which are axially contiguous to each other. The inner coil-set 24, in the embodiment as seen in FIGS. 2 and 3, has an internal diameter larger than that of the base arch wire, thus encircling the base arch wire, unrestrictedly, forming a freely functional helical spring. The diameter of the outer coil-set 26 is equal to or slightly smaller than that of the arch wire 16 so that the coil can readily slide or force fit over the arch wire and be held in frictional engagement with the wire. At least the terminal turn of the outer coil-set 26 is secured to the arch wire, as by soldering or welding. The connection being indicated by the numeral 28, firmly secures the torquing device 18 in its axial position on the base arch wire as well as anchoring the torquing device so that the apical loop can be readily deflected and resiliently activated.

Each of the coil-sets 24 and 26, forming the associated pair on each leg, are wound in the same direction with a common connecting turn; the associated coil-sets on one leg being wound in one direction while the corresponding pair of associated coil-sets on the other leg being wound in the opposite direction. This results in each leg 22 of the apical loop extending from its respective inner coil-set 24 in the same direction and on the same side of the base arch wire. Each of the coil-sets 24 and 26 in their respective pairs are wound uniformly thereby insuring a uniform action on each leg. In assembling the device on the base arch wire, it is positioned so that its apical loop usually is passively located parallel to the plane of the base arch wire, extending in the same direction as the extending distal ends of the base arch wire with its legs 22, emanating from the inner coil-sets 24, as indicated by dotted lines in FIG. 5 and subsequent Figures. Consequently, when the base arch wire is inserted into the bracket slots the device is activated by deflecting the apical loop in an upward direction, causing the inner coil-sets 24 to close-wind (e.g. rotate counter clockwise as seen in FIGS. 3 and 5). Thus, in activation the apical loop is deflected vertically to engage the cervical portion of the labial face of the crown of the tooth, causing the close-winding of the inner coil-sets of both legs to exert a uniform resilient spring action on the tooth.

The number of turns in each of the coil-sets 24 and 26 respectively may vary; however, it has been found that by winding each set with two or more turns sufficient material is allowed for the outer set to be soldered to the base arch wire, and allows sufficient wire in the inner coil-set to maintaining resilient spring action, while permitting a common connecting turn. Two or more turns in the inner coil-set have the following additional function. They allow for control of the load deflection characteristics since an increase in the number of coils results in lower forces per unit deflection and vice-versa. The spring may be preset or preloaded to a predetermined level of force by appropriately bending the legs of the apical loop to achieve a desired initial angular position in the passive state. The load can also be varied by changing the size of the diameter of the coils.

The operation of the device in providing lingual root movement is observed in FIGS. 3 and 4. As seen in FIG. 3, the legs 22 are curved inwardly toward the labial face of the tooth crown from a planar configuration so that only the top portion 20 of the apical loop will form a point or line contact with the cervical face of the tooth, thus concentrating the torquing force at a point of greatest mechanical advantage. Also, in this invention, the spring is anchored at points close to the point of application of the load rather than remotely as in other techniques, thus enhancing its effectiveness. In addition to other forces which may be applied on the tooth by or through the base arch wire, there is created by the present device, a force "couple" indicated by arrows $A^1$ and $A^2$ created on the tooth, resulting in pivoting of the root in the lingual direction as, indicated by arrow B in FIG. 4. During this movement the base arch wire may function in its conventional manner utilizing either class 2 elastics or headgear therapy to restrain the crowns of the maxillary denture and allowing only the desired root movement. Other reactive forces are distributed evenly over the supporting denture so that all harmful counter forces are minimized.

As the teeth most frequently requiring lingual root movement are the maxillary central incisors, the placement of the present device will not produce undue lateral expansive counter forces on the base arch wire, because the legs 22 extend vertically, substantially parallel to each other and are anchored at a point on the base arch wire close to the line of action of the apical loop. At this point it may be stated that while present device is employed, the orthodontist may undertake other suitable correctional procedure indicated at that time.

Upon placement of the loop on the denture, FIG. 3, a steady resilient movement is effected in the direction of arrow C (FIG. 5). The wire employed may be standard orthodontic spring wire of an appropriate diameter. The height of the loop may be varied in accordance with individual orthodontic requirements with regard to the anatomy of the tooth and the magnitude and point of application of the load. The actual spring rate of the spiral coil-set 24 can be selected by varying the number of coils, the size of the wire forming the coil and the diameter of the spiral. As a result the torque and deflection characteristics may be carefully controlled.

In the embodiment shown in FIGS. 1–6 and 9 and 10 the two coil-sets 24 and 26 are aligned along a common axis and are located on the arch wire coaxial with the longitudinal center of the arch wire. The diameter of the inner coil 24 should thus be sufficiently larger than the diameter of the arch wire 16 so as to permit at least a 90° deflection of the coil about the arch wire and still maintain the coil 24 spaced unrestrictedly from the base wire during activation. Preferably, it is desirable to dimension the inner diameter of the coil-set 24 so that it is movable in an are greater than 90° from its passive position without causing undue tightening of the helical spring or binding of the spring against the arch wire.

The point of force application of the apical loops is on the labial face of the crown of the tooth at a practical point most apically approaching the center of resistance for root movements. The device is so designed as to deliver moments of force in the optimal range for moving the roots with an action span in excess of 90° and at a low load deflection rate with no perceptible deformation of the spring wire. The spring biasing, as seen in FIGS. 5–12, results primarily from a counter-clockwise loading of the helical spring in conjunction with the displacement of the apical loop from the passive lingual position into the active apical position. Once loaded, the spring action remains dynamic throughout the treatment process, being free of binding with the base arch wire and therefore unrestricted by the base arch wire, the torque exerted on the tooth is continuous and constant, being applied even after the tooth has begun its movement. At no time does the spring action of the present device degrade or deaden and therefore its replacement, resetting, or adjustment need not be made with the frequency found with the use of prior devices.

The device 18 is attached to the base arch wire so that its legs 22 closely straddle the bracket 14 attached to the corresponding tooth. The legs will generally extend substantially normal to the plane of the base wire in the passive position and parallel to each other although they may be set to be non-parallel as required. The legs are usually mounted substantially parallel and close to the central vertical axis of the tooth on which the apical loops rests and the forces exerted by the device act primarily in the median plane of the treated tooth. Any reactive forces are distributed over the length of the arch wire and without excessive action on any one tooth.

The range of variations and sizes of brackets, used in any of the conventional orthodontic techniques, as well as the variation in sizes of teeth themselves is predictable, so that it is possible, in accordance with the present invention, to provide an arch wire having a generally preformed curvature on which a plurality of torquing devices 18 are secured in varying required positions. Thus, the orthodontist may be supplied with a readily available arch wire and torquing system which is already manufactured and assembled and which requires only placement in the patient's mouth, as indicated in FIG. 1. Should the preformed assembly contain excess torquing devices, one or more of them, may be removed by simply cutting the resilient wire so that only those necessary for selected teeth remain. Should one tooth require more torque than another the apical loop may be cut off when the desired movement is achieved, without the necessity of removing the base arch wire.

It will also be evident that the device may be altered in form so that the inner coil set of each pair of coils is attached or fixed to the base arch wire, while the outer coil set is unrestricted. Thus, although a reverse arrangement of the coils of each leg is obtained, the same dynamic function is preserved.

While conventional manufacturing methods may be employed to fabricate devices embodying the principles of the present invention, a further feature of the present invention lies in the provision of a simpler and more effective technique of fabrication. According to the present invention commercially available orthodontic wire may be employed. A suitable length sufficient for the formation of a loop and the contiguous coil sets at the end of each leg is provided. The ends of the loop are turned in a suitable sequence upon a two-step arbor or mandrel to form the coil sets. The shape and diameters of the steps of the arbor conform to that of the desired inner diameter of each of the contiguous coil sets. The sequence may provide the formation of the inner or outer sets on each of the two legs simultaneously, or separately on each leg, one after the other. Following formation of the coil sets on each leg the U-shaped loops are formed by bending the central section of the wire. The base arch wire is threaded through the coils of the apical loop and located at the proper position. The arch wire and coil sets are then fixed together by solder or other means. The two step modular arbor which is employed, coupled with the sequential turning of the coils, insures the achievement of the proper inner diameter and overall loop dimensions. Moreover, this achieves the proper direction of turning of the coils so that both legs of the apical loop and the contiguous coils sets act to close wind in a uniform manner when installed on the denture.

Another feature of the present invention involves the particular method of soldering the outer coil set of each leg to the base arch wire. This is achieved without damage to the spring or the base wire and utilizes only a minimal amount of orthodontic solder. As the smallest available orthodontic solder filament is 0.015 and the conventional torquing loop material is approx. 0.011 or 0.012, it is necessary to first cold draw such filament to a diameter approximating that of the apical loop spring. The solder is then formed into a coil or arc of the same internal diameter of the outer coil set of the apical loop. A single coil or arc is slipped over the base arch wire and placed adjacent to the last turn of the outer coil set of each leg. After carefully applying flux the solder is melted and a joint formed by conventional electrical resistance heating of the base arch wire, controlled to provide only sufficient heat to melt the solder and for only such time as required to cause the solder to flow. The utilization of controlled resistance heating and the use of minimal amounts of solder strategically placed, and in addition to the fact that only the outer coil set is in close contact to the base arch wire, results in an effective positive attachment without detrimental side effects. Empirically this procedure results in significantly reducing the heat requirement necessary to produce a firm bond between the apical loop and the base arch wire.

Several modifications of the structure of the present invention are shown herein. In FIGS. 9 and 10 a structure similar to that shown in FIGS. 1–3 is illustrated, except for the fact that the outer coil 26a is elliptical rather than circular in shape. Such a construction is particularly adapted for use on an arch wire which, as seen in FIG. 10, is rectangular in crosssection. The embodiment shown in FIGS. 9 and 10 does not require soldering or welding attachment to the arch wire, but is secured to the arch wire by forcing or sliding the elliptical coil 26a of the arch wire so that a secure binding is obtained with respect to the arch wire itself. Simultaneously, however, the inner coil set 24 which provides the spring action remains spaced from the arch wire and continues to be unrestricted, as previously described, so that it may thereafter be activated, as seen in FIGS. 9, 10. If desired, the elliptical outer coil 26a may be soldered to the rectangular arch wire as was done in the embodiment shown previously.

In FIGS. 7 and 8 still another embodiment is shown wherein the inner coil set 24a at the end of each of the legs 22 and the outer coil sets 26 are offset with respect to one another so that they do not lie along a common axis. The inner coil sets 24a of each leg are coaxial and are adapted to lie outside the arch wire 16. In this embodiment the device functions in the same manner as that described earlier.

In FIGS. 11 and 12 the features of FIGS. 7 and 8 are combined with those of FIGS. 9 and 10 to provide a device capable of attachment to a rectangular arch wire. This embodiment has the operation, function and virtue of each of the previous embodiments.

It will be seen from the foregoing that an improved lingual root torquing device, having the advantages enumerated herein is easily and simply obtained. The present invention is clearly advantageous in lingual root torquing of anterior teeth. However, it has similar use and advantage in torquing posterior teeth, lingually by placement along the more distal portions of the arch wire. Additionally, the present invention may be employed to produce buccal uprighting movements. To provide buccal root movement, the direction of the loop is reversed from the apical direction to the occlusal direction, with the legs emanating from the coaxial helical coil sets superior to the base arch wire so as to provide coil sets which close wind when placed against the denture. This provides a suitable torquing device having a loop which engages the tooth occlusally in relationship to the tooth bracket.

It will be apparent from the foregoing that various modifications and changes can be made to the basic content of the present invention without departing from its teachings. Accordingly, the present disclosure is intended to be illustrative only and not limiting of the scope of the invention.

What is claimed is:

1. An orthodontic torquing appliance for applying torquing forces to at least one tooth, comprising:
   an arch wire adapted to be secured to a surface of said at least one tooth; and
   at least one torquing device for applying a force to said surface of said tooth comprising a loop having a top central portion adapted to contact said surface of said tooth at a position spaced from said arch wire, and a pair of extending legs, each leg terminating in at least one force applying spring coil which is integral with its respective leg, each of said coils being unrestricted with respect to said arch wire; and means for fixedly and nonrotatably attaching the ends of said unrestricted coils, at portions thereof spaced from their respective legs, to said arch wire to be anchored against axial and rotary displacement relative to said arch wire.

2. The appliance according to claim 1 wherein said loop is substantially U-shaped and its legs extend substantially normal to the plane of the arch wire.

3. The appliance according to claim 1 wherein said legs are curved inwardly from a planar configuration.

4. The appliance according to claim 1 wherein said means for fixedly attaching said unrestricted coils to said arch wire includes further coils of smaller internal diameter than said unrestricted coils respectively coupled to said unrestricted coils, the further coils and their respective associated unrestricted coils lying adjacent to each other and having a common turn portion.

5. The appliance according to claim 3 wherein said coils are wound in a direction to provide closing action of the spring coils when said appliance is positioned on said tooth.

6. The appliance according to claim 1 wherein said coils each have axes lying substantially parallel to the arch wire.

7. The appliance according to claim 1 wherein said coils are helically wound in a common direction.

8. The appliance according to claim 5 wherein the axes of said coils are substantially coaxial with said arch wire and the internal diameter of said unrestricted coils is greater than that of the arch wire.

9. The appliance according to claim 1 including a plurality of said torquing devices secured to said arch wire and spaced along said arch wire corresponding to the position of selected teeth.

10. The appliance according to claim 1 wherein said further coil is substantially coaxial with said arch wire and the axes of said unrestricted coils are offset from the axis of said arch wire.

11. The appliance according to claim 1 wherein each coil includes a plurality of turns.

12. The appliance according to claim 1 wherein said means for fixedly attaching said unrestricted coils to said arch wire includes solder fixedly securing an end portion of each of said unrestricted coils to said arch wire.

13. The appliance according to claim 4 wherein said further coils are located axially outwardly of their associated unrestricted coils relative to said legs of said torquing device.

14. An orthodontic torquing appliance for applying torsional forces to at least one tooth, comprising:
  an arch wire having a non-circular cross-section adapted to be secured to a surface of said at least one tooth; and
  at least one torquing device for applying a force to said surface of said tooth comprising a loop having a top central portion adapted to contact said surface of said tooth at a position spaced from said arch wire, and a pair of extending legs, each leg terminating in first and second coil sets, the first coil set of each leg having a non-circular inner periphery adapted to bind positively and nonrotatably with said arch wire to prevent rotary displacement of said first coil set about said arch wire, and the second coil set of each leg including a force applying spring coil which is unrestricted with respect to said arch wire and which is interposed between its respective leg and first coil set.

15. The appliance according to claim 14 wherein said arch wire has a rectangular cross-section.

16. The appliance according to claim 14 wherein said first coil sets of each leg are axially slidable along said arch wire.

17. The appliance according to claim 14 wherein said loop is substantially U-shaped and its legs extend substantially normal to the plane of the arch wire.

18. The appliance according to claim 14 wherein said legs are curved inwardly from a planar configuration.

19. The appliance according to claim 14 wherein said first coil set has a smaller internal diameter than said unrestricted second coil set, and wherein said first and second coil sets of each leg lie adjacent to each other and have a common turn portion.

20. The applicance according to claim 18 wherein said second coil sets are wound in a direction to provide closing action of the spring coils when said appliance is positioned on said tooth.

21. The appliance according to claim 14 wherein said coil sets each have axes lying substantially parallel to the arch wire.

22. The appliance according to claim 14 wherein the coils of each set are helically wound in a common direction.

23. The appliance according to claim 14 wherein the axes of said coil sets are substantially coaxial with said arch wire and the internal diameter of each of said unrestricted coil sets is greater than that of the arch wire.

24. The appliance according to claim 14 including a plurality of said torquing devices secured to said arch wire and spaced along said arch wire corresponding to the position of selected teeth.

25. The appliance according to claim 14 wherein said first coil set is substantially coaxial with said arch wire and the axes of said second unrestricted coil sets are offset from the axes of said arch wire.

26. The appliance according to claim 14 wherein each coil set includes a plurality of turns.

27. A method for effecting the lingual tilting of the roots of at least one selected tooth in a denture, comprising:
  applying a band to at least one selected tooth in said denture,
  fixing a bracket to each of said bands,
  applying an arch wire to said brackets to extend about said denture;
  applying at least one torquing device on said arch wire in a position corresponding to said at least one selected tooth, said at least one torquing device comprising a U-shaped wire loop having a central portion adapted to engage the labial surface of said at least one selected tooth and a pair of extending legs, each leg terminating in at least one coil which is unrestricted with respect to said arch wire, and means for fixedly attaching said unrestricted coils, at portions thereof spaced from their respective legs, said coils being wound in directions so as to bias said legs in the same direction,
  rotating said wire loop about said arch wire in a direction to wind-up the coils about the arch wire to increase the biasing force of said coils on said legs in a direction toward the labial surface of the tooth, and
  releasing said wire loop to thereby apply a torquing force on said tooth about the point of attachment of the arch wire.

28. The appliance according to claim 1 wherein each of said force applying spring coils comprises a plurality of adjacent turns which are in direct contact with each other.

29. The appliance according to claim 14 wherein each of said force applying spring coils comprises a plurality of adjacent turns which are in direct contact with each other.

30. The method according to claim 27 wherein each leg terminates in at least one coil which has a plurality of adjacent turns, and comprising winding said coils such that side surfaces of said adjacent turns are in direct contact with each other.

* * * * *